(12) United States Patent
Huang et al.

(10) Patent No.: US 12,059,284 B2
(45) Date of Patent: Aug. 13, 2024

(54) LUNG CANCER PREDICTION

(71) Applicants: The Johns Hopkins University, Baltimore, MD (US); Provincial Health Services Authority, Vancouver (CA)

(72) Inventors: Peng Huang, Baltimore, MD (US); Yuliang Li, Baltimore, MD (US); Stephen Lam, Vancouver (CA)

(73) Assignees: THE JOHNS HOPKINS UNIVERSITY, Baltimore, MD (US); PROVINCIAL HEALTH SERVICES AUTHORITY, Vancouver (CA)

( * ) Notice: Subject to any disclaimer, the term of this patent is extended or adjusted under 35 U.S.C. 154(b) by 378 days.

(21) Appl. No.: 17/597,214

(22) PCT Filed: Jun. 23, 2020

(86) PCT No.: PCT/US2020/039139
§ 371 (c)(1),
(2) Date: Dec. 29, 2021

(87) PCT Pub. No.: WO2021/015913
PCT Pub. Date: Jan. 28, 2021

(65) Prior Publication Data
US 2022/0240881 A1 Aug. 4, 2022

Related U.S. Application Data

(60) Provisional application No. 62/877,210, filed on Jul. 22, 2019.

(51) Int. Cl.
*G06T 7/00* (2017.01)
*A61B 6/00* (2006.01)
(Continued)

(52) U.S. Cl.
CPC .............. *A61B 6/5211* (2013.01); *A61B 6/03* (2013.01); *A61B 6/5229* (2013.01); *G06N 3/045* (2023.01);
(Continued)

(58) Field of Classification Search
CPC ....... A61B 6/5211; A61B 6/03; A61B 6/5229; G16H 50/20; G06N 3/045; G06T 7/0016; G06T 2207/30064
See application file for complete search history.

(56) References Cited

U.S. PATENT DOCUMENTS

| | | | |
|---|---|---|---|
| 11,734,599 B2* | 8/2023 | Hao | A61B 6/5258 705/2 |
| 2018/0068083 A1* | 3/2018 | Cohen | G16B 40/30 |

(Continued)

FOREIGN PATENT DOCUMENTS

| | | | | |
|---|---|---|---|---|
| CN | 108876779 A | 11/2018 | | |
| CN | 109841281 A | 6/2019 | | |
| WO | WO-2021258081 A1 * | 12/2021 | ....... | G06F 18/24133 |
| WO | WO-2022249198 A1 * | 12/2022 | ............... | A61B 6/50 |

OTHER PUBLICATIONS

Ardila, Diego, et al. "End-to-end lung cancer screening with three-dimensional deep learning on low-dose chest computed tomography." Nature medicine 25.6 (2019): 954-961.*

(Continued)

*Primary Examiner* — Shefali D Goradia
(74) *Attorney, Agent, or Firm* — MH2 Technology Law Group LLP

(57) ABSTRACT

A device may obtain first information relating to one or more first lung nodules identified in first imaging of a chest of a patient and second information relating to one or more second lung nodules identified in second imaging of the chest of the patient. The device may provide the first information and the second information to a machine learn- (Continued)

ing model. The device may determine, using the machine learning model, a risk of lung cancer associated with the patient based on an elapsed time between performance of the first imaging and the second imaging and differences between the first information and the second information. The risk of lung cancer may have an inverse correlation to the elapsed time and a direct correlation to the differences. The device may perform one or more actions based on the risk of lung cancer that is determined 20 Claims, 7 Drawing Sheets

(51) Int. Cl.
*A61B 6/03* (2006.01)
*G06N 3/045* (2023.01)
*G16H 50/20* (2018.01)
(52) U.S. Cl.
CPC .......... *G06T 7/0016* (2013.01); *G16H 50/20* (2018.01); *G06T 2207/30064* (2013.01)

(56) References Cited

U.S. PATENT DOCUMENTS

2019/0087532 A1* 3/2019 Madabhushi .... G06V 30/19173
2021/0287795 A1* 9/2021 Declerck ................ G16H 30/20

OTHER PUBLICATIONS

Hawkins, Samuel, et al. "Predicting malignant nodules from screening CT scans." Journal of Thoracic Oncology 11.12 (2016): 2120-2128.*

International Search Report and Written Opinion issued in International Application No. PCT/US2020/039139; Dated Oct. 1, 2020.

Aberle, et al., "Reduced Lung-Cancer Mortality with Low-Dose Computed Tomographic Screening," New England Journal of Medicine, Aug. 4, 2011, vol. 365(5), pp. 395-409.

Tammemagi, et al., "Participant Selection for Lung Cancer Screening by Risk Modelling (The Pan-Canadian Early Detection of Lung Cancer[PanCan] Study): a Single-arm, Prospective Study," Lancet Oncol, 2017, vol. 18, pp. 1523-1531.

* cited by examiner

LUNG CANCER PREDICTION

CROSS-REFERENCE TO RELATED APPLICATIONS

This Patent Application is a 371 national stage of PCT Application PCT/US2020/039139 filed on Jun. 23, 2020, entitled "LUNG CANCER PREDICTION," which claims priority to U.S. Provisional Patent Application No. 62/877, 210, filed on Jul. 22, 2019, and entitled "LUNG CANCER PREDICTION," both of which are hereby expressly incorporated by reference herein.

BACKGROUND

Lung cancer is a malignant lung tumor characterized by uncontrolled cell growth in tissues of the lung. Lung cancer often appears as one or more pulmonary nodules visible on a chest radiograph.

SUMMARY

According to some implementations, a method may include obtaining, by a device, first information relating to one or more first lung nodules identified in first imaging of a chest of a patient and second information relating to one or more second lung nodules identified in second imaging of the chest of the patient, wherein the one or more first lung nodules and the one or more second lung nodules share at least one lung nodule, wherein the second imaging of the chest of the patient has been obtained a threshold period of time after the first imaging of the chest of the patient; providing, by the device, the first information and the second information to a machine learning model, wherein the machine learning model has been trained according to lung nodule data relating to lung nodules of a plurality of subjects, wherein the lung nodule data for a subject, of the plurality of subjects, has been weighted based on a duration between a first time when the lung nodule data was obtained for the subject and a second time when the subject was diagnosed with lung cancer; determining, by the device and using the machine learning model, a risk of lung cancer associated with the patient based on an elapsed time between performance of the first imaging and the second imaging and differences between the first information and the second information, wherein the risk of lung cancer has an inverse correlation to the elapsed time and a direct correlation to the differences; and performing, by the device, one or more actions based on the risk of lung cancer that is determined.

According to some implementations, a device may include one or more memories and one or more processors to obtain first information relating to one or more first lung nodules and one or more first disease conditions identified in first imaging of a chest of a patient and second information relating to one or more second lung nodules and one or more second disease conditions identified in second imaging of the chest of the patient; process the first information and the second information with a machine learning model to determine a risk of lung cancer associated with the patient based on an elapsed time between performance of the first imaging and the second imaging and differences between the first information and the second information, wherein the risk of lung cancer has an inverse correlation to the elapsed time and a direct correlation to the differences, wherein the machine learning model has been trained according to lung nodule data relating to lung nodules of a plurality of subjects and disease condition data relating to disease conditions of the plurality of subjects, wherein the lung nodule data and the disease condition data for a subject, of the plurality of subjects, has been weighted based on a duration between a first time when the lung nodule data and the disease condition data was obtained for the subject and a second time when the subject died due to lung cancer; and perform one or more actions based on the risk of lung cancer that is determined.

According to some implementations, a non-transitory computer-readable medium may store one or more instructions that, when executed by one or more processors, may cause the one or more processors to obtain first information relating to one or more first lung nodules identified in a first computed tomography (CT) scan of a chest of a patient, second information relating to one or more second lung nodules identified in a second CT scan of the chest of the patient, third information relating to an elapsed time between performance of the first CT scan and the second CT scan, and fourth information relating to at least one of an age of the patient, a gender of the patient, a smoking history of the patient, a family history of cancer associated with the patient, or an exposure of the patient to a carcinogen; process the first information, the second information, the third information, and the fourth information with a machine learning model to determine a risk of lung cancer associated with the patient based on the third information and the fourth information and differences between the first information and the second information; and perform one or more actions based on the risk of lung cancer that is determined.

DETAILED DESCRIPTION

Figure 1A:
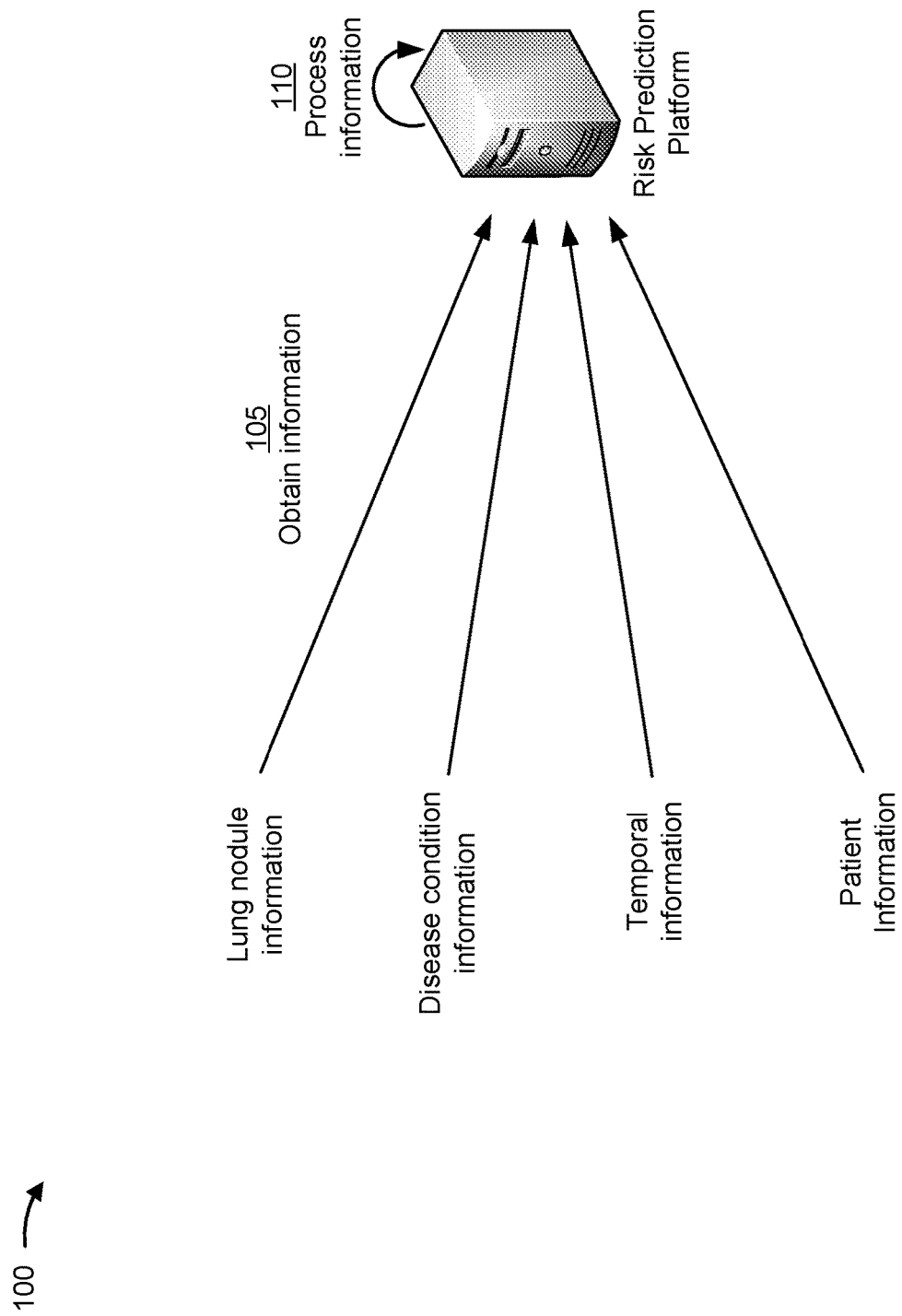
FIGS. 1A and 1B are diagrams of one or more example implementations described herein.

The following detailed description of example implementations refers to the accompanying drawings. The same reference numbers in different drawings may identify the same or similar elements.

Lung cancer in a patient may be identified by a chest imaging study followed by a pathological confirmation. In such cases, a radiologist, or another type of care provider, may examine one or more chest imaging studies of the patient to identify one or more lung nodules and record information relating to the lung nodules. A lung nodule present over consecutive imaging studies is at a higher malignancy risk when the lung nodule demonstrates an increase in diameter or an increase in density. Previous techniques attempt to identify a risk of lung cancer for a patient by observing changes in a diameter or a density of a largest lung nodule identified in chest radiographs. However, such techniques do not produce an accurate assessment of whether a patient may develop lung cancer in cases when the patient has multiple lung nodules. Furthermore, the previous techniques lack the ability to estimate an aggressiveness of the lung cancer or estimate an expected mortality associated with the lung cancer. Accordingly, such deficiencies may result in misdiagnoses or undetected malignancies, thereby resulting in otherwise-preventable morbidity and mortality, wasted healthcare resources, and/or the like.

According to some implementations described herein, a risk prediction platform may perform lung cancer prediction according to a machine learning model. In some implementations, the risk prediction platform may obtain baseline information (e.g., spatial information) relating to characteristics of one or more lung nodules (e.g., sizes, locations, densities, image textures, and/or the like) and/or one or more disease conditions (e.g., non-lung nodule disease conditions) identified in a baseline imaging (e.g., a CT scan) of a chest of a patient and may obtain subsequent information relating to characteristics of one or more lung nodules and/or one or more disease conditions identified in a subsequent imaging (e.g., a CT scan) of the chest of the patient (e.g., to permit comparison of how spatial characteristics of one or more lung nodules change over time and/or to permit comparison of how a disease condition changes over time). The risk prediction platform also may obtain temporal information relating to an elapsed time between the baseline imaging and the subsequent imaging. For example, the baseline imaging may precede the subsequent imaging by at least a threshold time period (e.g., 90 days, 180 days, 1 year, and/or the like). The risk prediction platform may further obtain patient information relating to the patient, such as an age of the patient, a gender of the patient, a smoking history of the patient, a family history of cancer associated with the patient, an exposure (e.g., an environmental exposure) of the patient to a carcinogen, and/or the like.

In some implementations, the risk prediction platform may process the baseline information, the subsequent information, the temporal information, and the patient information using a machine learning model. The machine learning model may be trained according to historical lung nodule data and disease condition data for a plurality of lung cancer subjects. Lung nodule data and/or disease condition data for a subject, of the lung cancer subjects, may be weighted based on how much time has elapsed between when the lung nodule data and/or disease condition data for the subject was obtained and when the subject was diagnosed with lung cancer and/or when the subject died due to lung cancer. The risk prediction platform may determine, using the machine learning model, a risk of lung cancer for the patient and a survival estimate for the patient. The determined risk of lung cancer may have an inverse correlation to the elapsed time between the baseline imaging and the subsequent imaging and a direct correlation to a degree of differences between the baseline information and the subsequent information.

In this way, the risk prediction platform facilitates lung cancer prediction with improved accuracy, thereby allowing for detection of lung cancer (e.g., aggressive lung cancer associated with mortality) that otherwise would not have been possible. Accordingly, the risk prediction platform conserves healthcare resources (e.g., care provider resources, imaging resources, diagnostic resources, computing resources, and/or the like) associated with misdiagnoses, as well as improves morbidity and mortality outcomes for patients. Furthermore, the risk prediction platform is able to provide a robust set of data that permits improved treatment of lung cancer and improved management of lung cancer risk. As a result, the risk prediction platform further conserves healthcare resources that may otherwise be used by unnecessary, or overly-aggressive, medical intervention.

Figure 1B:
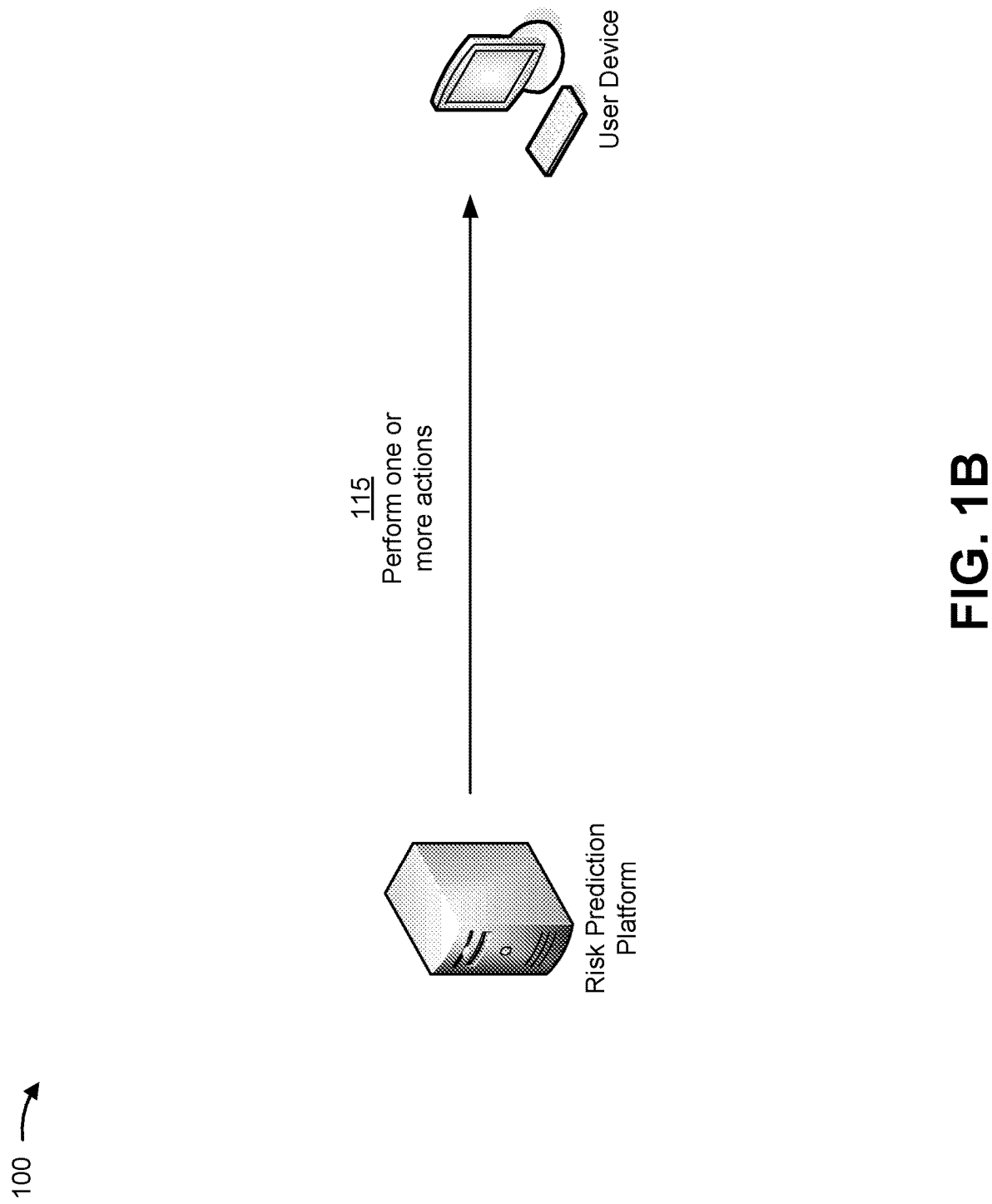

FIGS. 1A and 1B are diagrams of one or more example implementations 100 described herein. As shown in FIGS. 1A and 1B, example implementation(s) 100 may include a risk prediction platform and a user device. The risk prediction platform may be a computing device, a server, a cloud computing device, and/or the like that processes information relating to lung nodules and/or disease conditions identified in chest imaging, and determines a patient's risk of lung cancer or a patient's survival estimate based on the information. The risk prediction platform may be associated with an entity involved in researching cancers, diagnosing cancers, treating cancers, and/or the like. For example, the risk prediction platform may be associated with a hospital or a university.

The user device may be a computing device (e.g., a smartphone, a table computer, a laptop computer, a desktop computer, and/or the like), a service device, a cloud computing device, and/or the like that transmits, receives, and/or processes information relating to lung nodules and/or disease conditions identified in chest imaging, information relating to a patient's risk of lung cancer, and information relating to a patient's survival estimate. The user device may be associated with a care provider or an entity involved in researching cancers, diagnosing cancers, treating cancers, and/or the like. For example, the user device may be associated with a hospital, a radiologist or radiology practice, an oncologist or oncology practice, and/or the like.

As used herein, "imaging" may refer to an image (e.g., an X-ray, a CT scan, and/or the like) obtained by one or more radiography techniques, such as X-ray imaging, CT imaging (e.g., non-contrast CT imaging, contrast CT imaging, and/or the like), magnetic resonance imaging (MM), positron-emission tomography (PET) imaging, and/or the like. In some implementations, the imaging described herein may be chest imaging that depicts an area below a neck of a patient and above a bowel of the patient. In such a case, the chest imaging may depict a cardiovascular system and/or a pulmonary system of the patient. For example, the chest imaging may depict lungs of the patient.

As shown in FIG. 1A, and by reference number 105, the risk prediction platform may obtain information relating to a patient. In some implementations, the risk prediction platform may obtain lung nodule information relating to the patient. The lung nodule information may relate to one or more lung nodules (e.g., non-calcified lung nodules) identified in a baseline imaging (e.g., a first imaging) of a chest of the patient and one or more lung nodules identified in a subsequent imaging (e.g., a second imaging) of the chest of the patient. The one or more lung nodules identified in the baseline imaging may be included in the one or more lung nodules identified in the subsequent imaging. Additionally, or alternatively, the one or more lung nodules identified in the baseline imaging and the one or more lung nodules identified in the subsequent imaging may share at least one lung nodule.

The baseline imaging and the subsequent imaging may be consecutive imagings (i.e., no intervening imaging of the chest of the patient occurred between the imaging and the previous imaging) or non-consecutive imagings. Moreover, the subsequent imaging may be obtained a threshold period of time after the baseline imaging. The threshold period of time may be, for example, from 90 days to 2 years (e.g., 180 days, 1 year, and/or the like). In some implementations, the techniques described herein may be performed iteratively as additional subsequent imaging is obtained. For example, the techniques described herein may be performed a first time using first imaging as the baseline imaging and second imaging as the subsequent imaging, performed a second time using the second imaging as the baseline imaging and third imaging as the subsequent imaging, and so forth.

The lung nodule information may identify a size of a lung nodule, a shape of a lung nodule, an attenuation of a lung nodule, a margin of a lung nodule, a density of a lung nodule, a presence or an absence of a lung nodule, a quantity of lung nodules, and/or the like. For example, the lung nodule information may identify a quantity of lung nodules (e.g., non-calcified solid, ground glass opacity, or partial-solid lung nodules) present in the baseline imaging that are absent from the subsequent imaging, and/or a quantity of lung nodules present in the subsequent imaging that are absent from the baseline imaging. As another example, the lung nodule information may identify a quantity of lung nodules (e.g., non-calcified lung nodules) that are present in the baseline imaging and/or a quantity of lung nodules present in the subsequent imaging. A quantity of lung nodules may relate only to lung nodules that satisfy a threshold size (e.g., 4 mm).

In some implementations, the lung nodule information may identify a location of a lung nodule in a lung of the patient (e.g., right upper lobe, right middle lobe, right lower lobe, left upper lobe, lingula, left lower lobe, mediastinum, a location defined by a bronchial tree, and/or the like). Additionally, or alternatively, the lung nodule information may identify a diameter of a lung nodule, an attenuation or a density distribution of a lung nodule, a volume of a lung nodule, an image texture feature from within, surrounding, or outside of a lung nodule (e.g., based on two-dimensional and/or three-dimensional first and second order statistics, margin, shape, compactness, energy, entropy, grey level co-occurrence matrix features, grey level run length matrix features, wavelet features, and/or the like).

In some implementations, the risk prediction platform may obtain lung nodule information (e.g., spatial information) relating to a nodule's intra-nodular features, peri-nodular features, and/or extra-nodular features. Intra-nodular features may relate to a nodule's volume, longest diameter, shape, density (e.g., percent solid/ground-glass, tumor disappearance rate, cavity, fat, calcification, air bronchogram or bronchus cut-off, and/or the like), size, margin (e.g., irregular, lobulation, well-circumscribed, and/or the like), and/or the like. Peri-nodular features may relate to a nodule's spiculation, halo-sign, vessel convergence sign, and/or the like. Extra-nodular features may relate to a nodule's location (e.g., central or peripheral), pleural effusion, mediastinal/hilar adenopathy, emphysema, fibrosis (reticular/reticulonodular opacities or honeycombing, and/or the like), pleural tag or pleural thickening, distortion of adjacent lung parenchyma, chest wall or mediastinal invasion, and/or the like.

In some implementations, the risk prediction platform may obtain lung nodule information (e.g., spatial information, such as relating to size, location, attenuation, and/or spiculated margin) for each lung nodule (e.g., each lung nodule that satisfies a threshold size, such as 4 mm, and/or each non-calcified lung nodule) identified in the subsequent imaging. Moreover, the risk prediction platform may obtain lung nodule information (e.g., spatial information, such as relating to size, location, attenuation, and/or spiculated margin) for each lung nodule present in the baseline imaging that is also present in the subsequent imaging.

In other words, the risk prediction platform may obtain subsequent lung nodule information (e.g., spatial information) for each lung nodule of a set of lung nodules present in the subsequent imaging (e.g., relating to size, location, attenuation, shape, and/or spiculated margin at a time of the subsequent imaging) and may obtain baseline lung nodule information (e.g., spatial information) for each lung nodule of a set of lung nodules present in both the subsequent imaging and the baseline imaging (e.g., relating to size, location, attenuation, shape, and/or spiculated margin at a time of the baseline imaging). In some implementations, the lung nodule information may further identify whether a density of a lung nodule increased from the baseline imaging to the subsequent imaging. In this way, the risk prediction platform obtains lung nodule information that permits a comparison of lung nodules present in the baseline imaging and the subsequent imaging in order to identify changes in a lung nodule's spatial features (e.g., intra-nodular features, peri-nodular features, and/or extra-nodular features) over time.

In some implementations, the risk prediction platform may obtain disease condition information relating to the patient. The disease condition information may relate to one or more disease conditions (e.g., non-lung nodule disease conditions) identified in the baseline imaging of the chest of the patient (e.g., the baseline imaging used to identify the lung nodule information) and one or more disease conditions identified in the subsequent imaging of the chest of the patient (e.g., the subsequent imaging used to identify the lung nodule information), as described above. In other words, the lung nodule information and the disease condition information may be identified from the same baseline imaging and subsequent imaging. In this way, the risk prediction platform obtains disease condition information that permits identification of relationships between lung nodules and disease conditions.

The disease condition information may identify whether a disease condition is present (e.g., the baseline imaging and/or the subsequent imaging shows the disease condition) or is absent (e.g., the baseline imaging and/or the subsequent imaging does not show the disease condition). The disease condition information also may identify whether a disease condition has worsened from the baseline imaging to the subsequent imaging. In some implementations, the disease condition information may identify whether emphysema is present in the baseline imaging, whether emphysema is present in the subsequent imaging, and/or whether emphysema present in the subsequent imaging has worsened from the baseline imaging. Additionally, or alternatively, the disease condition information may identify whether cardiovascular abnormality (e.g., thoracic aortic aneurysm, aortic dissection, marked cardiomegaly, pulmonary hypertension, coronary artery calcifications, valvular calcifications, and/or the like) is present in the baseline imaging, whether cardiovascular abnormality is present in the subsequent imaging, and/or whether cardiovascular abnormality present in the subsequent imaging has worsened from the baseline imaging.

In other words, the risk prediction platform may obtain baseline disease condition information and subsequent disease condition information. In this way, the risk prediction platform obtains disease condition information that permits a comparison of disease conditions present in the baseline imaging and/or the subsequent imaging in order to identify an onset of a disease condition, a worsening of a disease condition over time, and/or the like.

In some implementations, the risk prediction platform may obtain temporal information relating to the patient. For example, the risk prediction platform may obtain temporal information relating to the baseline imaging and/or the subsequent imaging. The temporal information may identify an elapsed time (e.g., in days) between performance of the baseline imaging and performance of the subsequent imaging. In this way, the risk prediction platform obtains temporal information that permits time-based assessment of differences (e.g., spatial changes in lung nodule characteristics and/or disease conditions) between the baseline imaging and the subsequent imaging.

In some implementations, the risk prediction platform may obtain patient information relating to the patient. The patient information may include demographic information relating to the patient. For example, the patient information may identify an age of the patient at a time of the baseline imaging and/or the subsequent imaging, a gender of the patient, whether the patient has a family history of lung cancer, and/or the like. In addition, the patient information may include smoking history information relating to the patient. For example, the patient information may identify whether the patient is a current smoker, whether the patient is a former smoker, an age at which the patient began smoking, an age at which the patient quit smoking, an average daily quantity of cigarettes smoked by the patient, a quantity of years for which the patient has smoked, whether the patient currently resides with a smoker, whether the patient formerly resided with a smoker, and/or the like. Moreover, the patient information may include information identifying whether the patient has been exposed to one or more carcinogens (e.g., arsenic, asbestos, radon, and/or the like). In this way, the risk prediction platform obtains patient information that permits identification of lung cancer risk and/or survival time associated with particular patient groups, particular patient characteristics, and/or the like.

In some implementations, such as when the patient has had surgery associated with a lung cancer diagnosis, the risk prediction platform may obtain pathological information relating to the patient's primary tumor. For example, the risk prediction platform may obtain pathological information that provides an indication of a tumor TNM stage (e.g., stage IA, stage IB, stage IIA, and/or the like), tumor grade (e.g., well-differentiated, moderate, poorly-differentiated, undifferentiated, and/or the like), a tumor subtype (e.g., adenocarcinoma, squamous cell carcinoma, small cell carcinoma, and/or the like), a tumor histology (e.g., invasive carcinoma, metastasis, carcinoma in situ, and/or the like), and/or the like.

In some implementations, the risk prediction platform may provide a user interface, which may be used (e.g., by a hospital, a radiologist, an oncologist, a pulmonologist, a surgeon, a care provider, and/or the like) to enter the information relating to the patient (e.g., the lung nodule information, the disease condition information, the temporal information, and/or the patient information). The user interface may include one or more fields that permit users to provide inputs. For example, the one or more fields may permit a user to identify the lung nodule information, identify the disease condition information, identify the temporal information, identify the patient information, and/or the like.

In some implementations, the risk prediction platform may automatically obtain the information relating to the patient (e.g., the lung nodule information, the disease condition information, the temporal information, and/or the patient information). For example, the risk prediction platform may have access (e.g., via an application programming interface) to a computer system associated with a hospital, a radiology practice, and/or the like, and the risk prediction platform may obtain information from the computer system at regular intervals, upon a triggering event (e.g., information relating to the patient being entered into the computer system), and/or the like.

In some implementations, the risk prediction platform may obtain the information relating to the patient (e.g., the lung nodule information or the disease condition information) using a computer vision technique. For example, the risk prediction platform may obtain imaging of the chest of the patient (e.g., the baseline imaging and/or the subsequent imaging) and perform a computer vision technique on the imaging in order to identify and characterize lung nodules and/or disease conditions present in the imaging. In one such case, the risk prediction platform may be associated with an imaging device (e.g., an X-ray machine, a CT scanner, and/or the like) and may perform the computer vision technique on imaging captured by the imaging device (e.g., in real time).

The computer vision technique may include a convolutional neural network technique that identifies and characterizes lung nodules and/or disease conditions based on shapes, edges, colorations, patterns, locations, and/or the like. In some cases, the computer vision technique may include using an image recognition technique (e.g., an Inception framework, a ResNet framework, a Visual Geometry Group (VGG) framework, and/or the like), an object detection technique (e.g. a Single Shot Detector (SSD) framework, a You Only Look Once (YOLO) framework, and/or the like), and/or the like.

As shown by reference number 110, the risk prediction platform may process the information relating to the patient. For example, the risk prediction platform may process the information relating to the patient (e.g., the lung nodule information, the disease condition information, the temporal information, and/or the patient information) with a machine learning model. The risk prediction platform may train the machine learning model to recognize patterns in temporal changes and/or spatial changes of lung nodules, as well as relationships between lung nodules and disease conditions. The risk prediction platform may train the machine learning model according to historical data relating to lung cancer subjects. The historical data may include lung nodule data, disease condition data, and/or demographic data for each subject of the lung cancer subjects. In some implementations, the historical data may include pathological data, similar to that described above in connection with the pathological information, for each subject that received surgical intervention associated with lung cancer.

The lung nodule data may relate to lung nodules of a subject. For example, the lung nodule data may relate to one or more lung nodules identified in a baseline imaging of a chest of the subject and/or one or more lung nodules identified in a subsequent imaging of the chest of the subject. The lung nodule data may identify a quantity of lung nodules, spatial features of a lung nodule (e.g., intra-nodular features, such as volume, longest diameter, shape, density, size, entropy, and/or the like, peri-nodular features, such as spiculation, halo sign, vessel involvement, and/or the like, and/or extra-nodular features, such as pleural effusion, pleural thickening, distortion of adjacent lung parenchyma, and/or the like), a location of a lung nodule, and/or the like, in a manner similar to that described above in connection with the lung nodule information. The lung nodule data further may identify an elapsed time between the baseline imaging of the chest of the subject and the subsequent imaging of the chest of the subject.

The disease condition data may relate to disease conditions of the subject. For example, the disease condition data may relate to one or more disease conditions (e.g., non-lung nodule disease conditions) identified in the baseline imaging of the chest of the subject and/or one or more disease conditions identified in the subsequent imaging of the chest of the subject. The disease condition data may identify a presence of a disease condition, an absence of a disease condition, a worsening of a disease condition, and/or the like, in a manner similar to that described above in connection with the disease condition information. The disease condition data further may identify the elapsed time between the baseline imaging of the chest of the subject and the subsequent imaging of the chest of the subject.

The demographic data may relate to the subject associated with the lung nodule data and/or the disease condition data. The demographic data may identify an age of the subject, a gender of the subject, a family history of lung cancer associated with the subject, a smoking history associated with the subject, an exposure (e.g., an environmental exposure) of the subject to one or more carcinogens, and/or the like, in a manner similar to that described above in connection with the patient information.

The risk prediction platform further may train the machine learning model according to weighting data associated with the historical data for each subject of the lung cancer subjects. The weighting data for a subject may be based on diagnosis data and/or mortality data associated with the subject (e.g., based on survival analysis of diagnosis data and/or mortality data associated with the subject).

The diagnosis data may relate to a lung cancer diagnosis for the subject. For example, the diagnosis data may identify a duration between a first time when the lung nodule data and/or the disease condition data was obtained for the subject and a second time when the subject was diagnosed with lung cancer. The diagnosis data may identify a first duration associated with an elapsed time between the baseline imaging and the lung cancer diagnosis and a second duration associated with an elapsed time between the subsequent imaging and the lung cancer diagnosis.

The mortality data may relate to a death of the subject. For example, the mortality data may identify a duration between a first time when the lung nodule data and/or the disease condition data was obtained for the subject and a second time when the subject died due to lung cancer. The mortality data may identify a first duration associated with an elapsed time between the baseline imaging and the death of the subject and a second duration associated with an elapsed time between the subsequent imaging and the death of the subject.

The weighting data may relate to a weighting assigned to the historical data (e.g., the lung nodule data, the disease condition data, and/or the demographic data) of the subject based on the diagnosis data and/or the mortality data. The weighting may be based on one or more durations associated with the lung cancer diagnosis of the subject and/or one or more durations associated with the death of the subject due to lung cancer. Accordingly, a higher weighting may be assigned to historical data when one or more durations are relatively short (e.g., below a threshold value) and a lower weighting may be assigned to historical data when one or more durations are relatively long (e.g., above a threshold value). In this way, the weighting data provides an indication of a relevance of the lung nodule data and/or the disease condition data based on a degree of correlation of the lung nodule data and/or the disease condition data with lung cancer and/or death, thereby improving a predictive ability of the risk prediction platform.

Based on the historical data and associated weighting data, the risk prediction platform may determine that past characteristics of lung nodules and/or disease conditions are associated with a threshold probability of being associated with lung cancer and/or death. In some implementations, the risk prediction platform may use a scoring system (e.g., with relatively high scores and/or relatively low scores) to identify and/or classify characteristics as being associated with one another. In this case, the risk prediction platform may determine that a relatively high score is to be assigned to characteristics that are determined to be the same as or similar to previously identified characteristics (or more frequently identified than past identified characteristics). In contrast, the risk prediction platform may determine that a relatively low score is to be assigned to characteristics that are determined to be different than past identified characteristics (or less frequently identified than past identified characteristics).

The risk prediction platform may process the information relating to the patient, using the machine learning model, to determine a risk of lung cancer associated with the patient and/or a survival estimate associated with the patient. For example, the risk prediction platform, using the machine learning model, may determine the risk of lung cancer and/or the survival estimate based on the temporal information (e.g., an elapsed time between performance of the baseline imaging and the subsequent imaging), the patient information, the lung nodule information (e.g., differences between lung nodule information (e.g., spatial information) associated with the baseline imaging and lung nodule information (e.g., spatial information) associated with the subsequent imaging), and/or the disease condition information (e.g., differences between disease condition information associated with the baseline imaging and disease condition information associated with the subsequent imaging).

Differences between lung nodule information (e.g., spatial information) associated with the baseline imaging and lung nodule information (e.g., spatial information) associated with the subsequent imaging may relate to a degree by which a lung nodule has increased in size, a degree by which a lung nodule has increased in density, a lung nodule's development of a spiculated margin, and/or the like. Differences between disease condition information associated with the baseline imaging and disease condition information associated with the subsequent imaging may relate to a development of a disease condition, a worsening of a disease condition, a degree by which a disease condition has worsened, and/or the like.

The risk of lung cancer that is determined by the risk prediction platform may have an inverse correlation to an elapsed time between performance of the baseline imaging and the subsequent imaging, a direct correlation to the differences between lung nodule information associated with the baseline imaging and lung nodule information associated with the subsequent imaging, and a direct correlation to differences between disease condition information associated with the baseline imaging and disease condition information associated with the subsequent imaging. For example, the risk prediction platform may determine a lower risk of lung cancer based on a greater elapsed time between the baseline imaging and the subsequent imaging. As another example, the risk prediction platform may determine a higher risk of lung cancer based on greater differences (e.g., a greater quantity of differences, a greater degree of differences, and/or the like) between lung nodule information associated with the baseline imaging and lung nodule information associated with the subsequent imaging.

The risk prediction platform may determine the risk of lung cancer associated with the patient as, for example, a percentage (e.g., 0-100%), a probability (e.g., 0-1), or an expected time (e.g., in months) until a lung cancer diagnosis (e.g., calculated from the subsequent imaging). Moreover, the risk prediction platform may determine a plurality of risks of lung cancer associated with the patient. For example, each risk of lung cancer, of the plurality of risks of lung cancer, may relate to respective periods of time calculated from the subsequent imaging. As an example, the risk prediction platform may determine, for the patient, a first risk of lung cancer within 1 year from the subsequent imaging, a second risk of lung cancer within 2 years from the subsequent imaging, a third risk of lung cancer within 3 years from the subsequent imaging, and/or the like.

The risk prediction platform may determine the survival estimate (e.g., a lung cancer-free survival probability over a time period) associated with the patient as a survival curve. The survival curve may identify a percentage chance, or a probability, that the patient will be free of lung cancer at a plurality of future time points. For example, the survival curve may identify a percentage chance, or a probability, that the patient will not develop lung cancer from a time associated with the subsequent imaging until a future time (e.g., 1 year, 2 years, 3 years, and/or the like). In some implementations, the survival curve may be a Kaplan-Meier curve representing probabilities that the patient will be free of lung cancer over a time period and associated point-wise confidence intervals (e.g., 95% confidence intervals). In some implementations, the risk prediction platform may determine a restricted mean survival time for the patient based on a survival curve (e.g., based on an area under the survival curve).

In some implementations, the risk prediction platform may determine a mortality estimate (e.g., if the patient has received surgery associated with lung cancer) associated with the patient as a mortality curve. The mortality curve may identify a percentage chance, or a probability, that the patient will die due to lung cancer at a plurality of future time points. For example, the mortality curve may identify a percentage chance, or a probability, that the patient will die due to lung cancer from a time associated with the subsequent imaging until a future time (e.g., 2 years, 3 years, 5 years, and/or the like). The risk prediction platform may determine the mortality estimate according to the lung nodule information, as described herein, and/or a primary tumor's pathological information (e.g., a tumor TNM stage, a tumor subtype, a tumor histology, and/or the like).

As shown in FIG. 1B, and by reference number 115, the risk prediction platform may perform one or more actions based on determining the risk of lung cancer associated with the patient and/or the survival estimate associated with the patient. For example, the risk prediction platform may transmit information identifying the risk of lung cancer and/or information identifying the survival estimate to the user device. In some implementations, the risk prediction platform may generate and provide, to the user device, a user interface that includes information identifying the risk of lung cancer and/or information identifying the survival estimate. For example, the user interface may include a visual representation of a survival curve associated with the patient.

In some implementations, the risk prediction platform may determine a recommendation for an action based on the risk of cancer and/or the survival estimate (e.g., a survival curve) determined by the risk prediction platform (e.g., a recommendation associated with an invasive diagnostic test (e.g., lung biopsy), an invasive treatment (e.g., lung surgery, radiotherapy, chemotherapy, and/or the like), or for a follow-up imaging).

The recommendation may be based on a degree of the determined risk of cancer. In such a case, the risk prediction platform may recommend a first action when the degree of the risk of cancer falls within a first range (e.g., 0.2-0.4), and may recommend a second action when the degree of the risk of cancer falls within a second range (e.g., 0.4-0.6). Additionally, or alternatively, the risk prediction platform may recommend a first action or a second action based on whether the degree of the risk of cancer satisfies a threshold value (e.g., 0.3).

The recommendation may be based on a shape of a survival curve determined by the risk prediction platform. In such a case, the risk prediction platform may recommend a first action (e.g., a conservative follow up) if the survival curve (e.g., the entire survival curve) satisfies a threshold value (e.g., 0.99), recommend a second action (e.g., an immediate action, such as biopsy, surgery, or radiotherapy) if the survival curve transitions from above a threshold value to below the threshold value (e.g., 0.3) within a particular period of time (e.g., 6 months, 1 year, and/or the like), and/or recommend a third action (e.g., a 3-month follow-up, a 6-month follow-up, a 12-month follow-up, an 18-month follow-up, a 24-month follow-up, and/or the like) based on the survival curve transitioning from above a threshold value to below the threshold value (e.g., 0.8). Additionally, or alternatively, the risk prediction platform may recommend a first action or a second action based on whether the survival curve is between a particular interval, based on a rate of change of a slope associated with the survival curve change, and/or the like. The risk prediction platform may transmit information identifying the recommendation to the user device, in a manner similar to that described above.

In this way, the risk prediction platform facilitates selective lung cancer intervention and follow up strategy for the patient based on the risk of lung cancer associated with the patient and/or the survival estimate associated with the patient. For example, treatment and other interventions may be deferred or eliminated for the patient when the risk of lung cancer is low, thereby reducing treatment-induced morbidity and mortality as well as conserving healthcare resources. Moreover, the risk prediction platform allows for early diagnosis of aggressive early-stage lung cancers (e.g., stage I lung cancers) to permit allocation of healthcare resources to patients who can most benefit from early lung cancer treatment. Furthermore, treatment and other interventions for a patient at high risk may be efficiently selected and scheduled based on the survival estimate determined by the risk prediction platform. In addition, the risk prediction platform provides lung cancer prediction with improved accuracy, thereby improving patient outcomes and reducing morbidity and mortality associated with misdiagnoses or undetected malignancy.

As indicated above, FIGS. 1A and 1B are provided merely as one or more examples. Other examples may differ from what is described with regard to FIGS. 1A and 1B.

Figure 2:
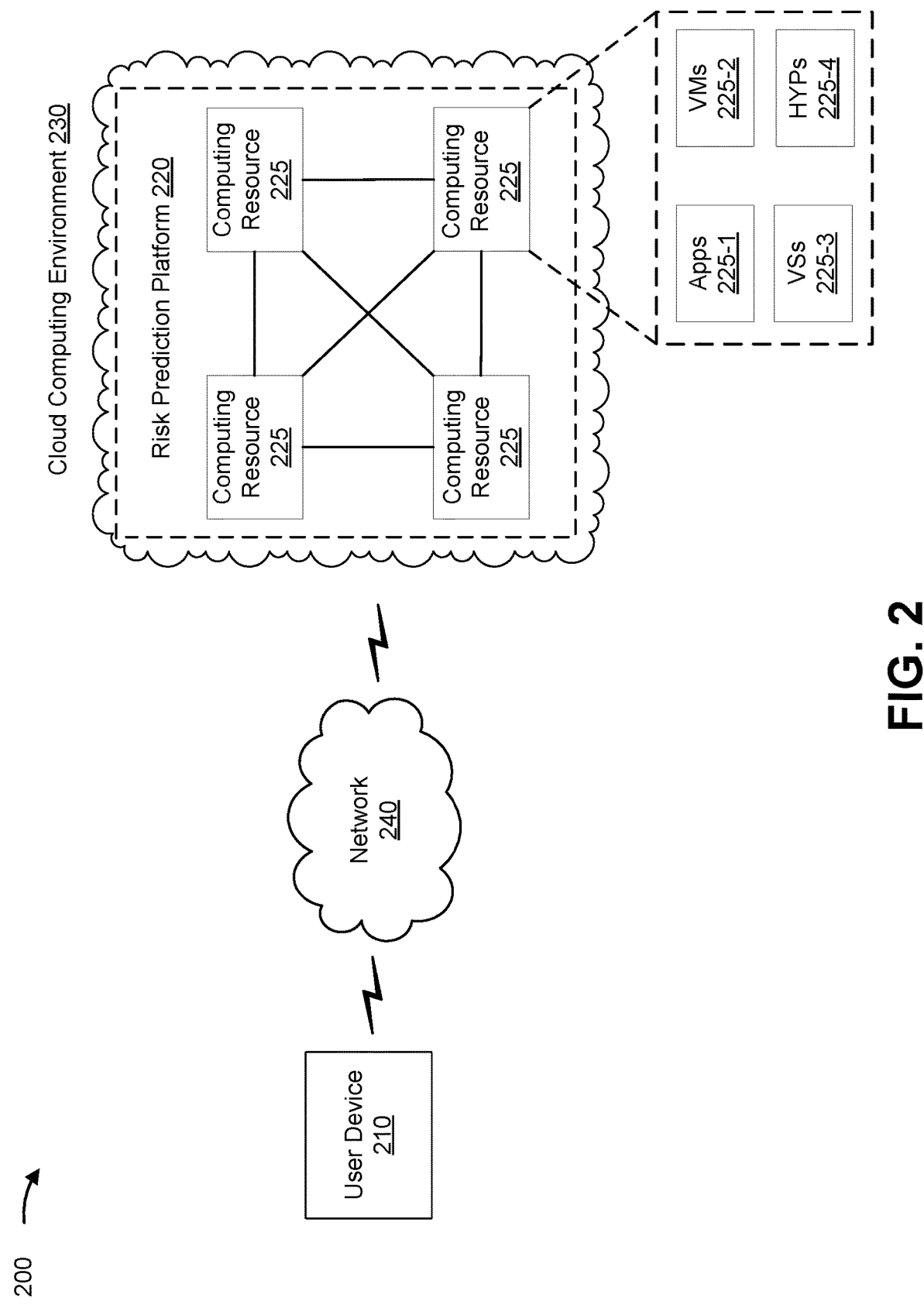
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a user device 210, a risk prediction platform 220, a computing resource 225, a cloud computing environment 230, and a network 240. Devices of environment 200 may interconnect via wired connections, wireless connections, or a combination of wired and wireless connections.

User device 210 includes one or more devices capable of receiving, generating, storing, processing, and/or providing information relating to a patient (e.g., lung nodule information, disease condition information, temporal information, patient information, and/or the like), information relating to a risk of lung cancer associated with a patient, information relating to a survival estimate associated with a patient, and/or the like. For example, user device 210 may include a communication and/or a computing device, such as a mobile phone (e.g., a smart phone, a radiotelephone, and/or the like), a laptop computer, a tablet computer, a handheld computer, a desktop computer, a gaming device, a wearable communication device (e.g., a smart wristwatch, a pair of smart eyeglasses, and/or the like), or a similar type of device. In some implementations, user device 210 may be a computing device (e.g., a server device) associated with an imaging device, a hospital, a radiology practice, an oncology practice, a surgery practice, and/or the like.

Risk prediction platform 220 includes one or more computing resources assigned to obtain information relating to a patient and process the information. For example, risk prediction platform 220 may be a platform implemented by cloud computing environment 230 that may obtain information relating to a patient, process the information using a machine learning model, determine a risk of cancer and/or a survival estimate associated with the patient, and/or the like. In some implementations, risk prediction platform 220 is implemented by computing resources 225 of cloud computing environment 230.

Risk prediction platform 220 may include a server device or a group of server devices. In some implementations, risk prediction platform 220 may be hosted in cloud computing environment 230. Notably, while implementations described herein may describe risk prediction platform 220 as being hosted in cloud computing environment 230, in some implementations, risk prediction platform 220 may be non-cloud-based or may be partially cloud-based.

Cloud computing environment 230 includes an environment that delivers computing as a service, whereby shared resources, services, and/or the like may be provided to user device 210, or the like. Cloud computing environment 230 may provide computation, software, data access, storage, and/or other services that do not require end-user knowledge of a physical location and configuration of a system and/or a device that delivers the services. As shown, cloud computing environment 230 may include risk prediction platform 220 and computing resource 225.

Computing resource 225 includes one or more personal computers, workstation computers, server devices, or another type of computation and/or communication device. In some implementations, computing resource 225 may host risk prediction platform 220. The cloud resources may include compute instances executing in computing resource 225, storage devices provided in computing resource 225, data transfer devices provided by computing resource 225, and/or the like. In some implementations, computing resource 225 may communicate with other computing resources 225 via wired connections, wireless connections, or a combination of wired and wireless connections.

As further shown in FIG. 2, computing resource 225 may include a group of cloud resources, such as one or more applications ("APPs") 225-1, one or more virtual machines ("VMs") 225-2, virtualized storage ("VSs") 225-3, one or more hypervisors ("HYPs") 225-4, or the like.

Application 225-1 includes one or more software applications that may be provided to or accessed by user device 210, or the like. Application 225-1 may eliminate a need to install and execute the software applications on user device 210, or the like. For example, application 225-1 may include software associated with risk prediction platform 220 and/or any other software capable of being provided via cloud computing environment 230. In some implementations, one application 225-1 may send/receive information to/from one or more other applications 225-1, via virtual machine 225-2.

Virtual machine 225-2 includes a software implementation of a machine (e.g., a computer) that executes programs like a physical machine. Virtual machine 225-2 may be either a system virtual machine or a process virtual machine, depending upon use and degree of correspondence to any real machine by virtual machine 225-2. A system virtual machine may provide a complete system platform that supports execution of a complete operating system ("OS"). A process virtual machine may execute a single program and may support a single process. In some implementations, virtual machine 225-2 may execute on behalf of a user, and may manage infrastructure of cloud computing environment 230, such as data management, synchronization, or long-duration data transfers.

Virtualized storage 225-3 includes one or more storage systems and/or one or more devices that use virtualization techniques within the storage systems or devices of computing resource 225. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 225-4 provides hardware virtualization techniques that allow multiple operating systems (e.g., "guest operating systems") to execute concurrently on a host computer, such as computing resource 225. Hypervisor 225-4 may present a virtual operating platform to the guest operating systems and may manage the execution of the guest operating systems. Multiple instances of a variety of operating systems may share virtualized hardware resources.

Network 240 includes one or more wired and/or wireless networks. For example, network 240 may include a cellular network (e.g., a long-term evolution (LTE) network, a code division multiple access (CDMA) network, a 3G network, a 4G network, a 5G network, another type of next generation network, and/or the like), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The quantity and arrangement of devices and networks shown in FIG. 2 are provided as one or more examples. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices)

of environment 200 may perform one or more functions described as being performed by another set of devices of environment 200.

Figure 3:
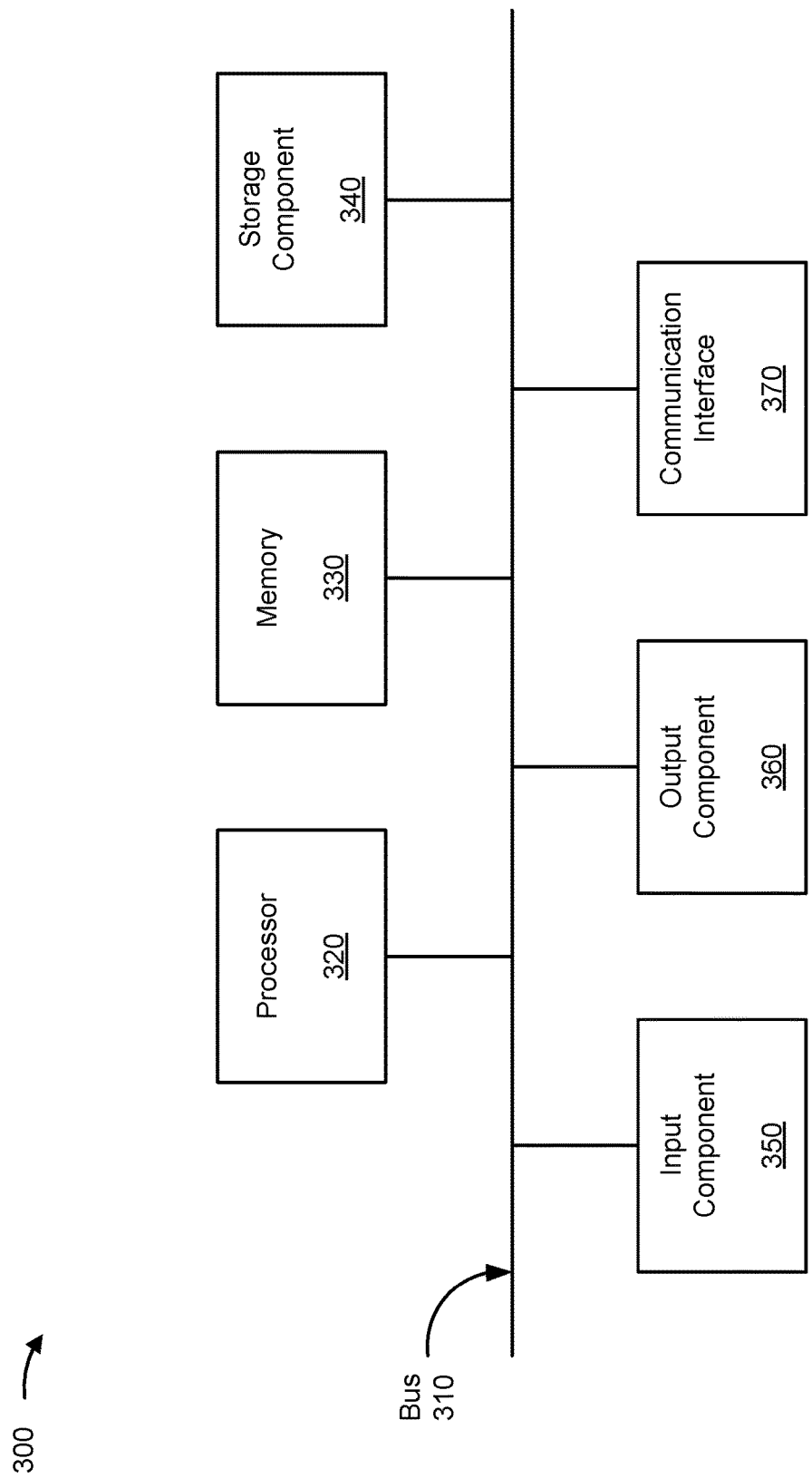
FIG. 3 is a diagram of example components of one or more devices of FIG. 2.

FIG. 3 is a diagram of example components of a device 300. Device 300 may correspond to user device 210, risk prediction platform 220, and/or computing resource 225. In some implementations, user device 210, risk prediction platform 220, and/or computing resource 225 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among multiple components of device 300. Processor 320 is implemented in hardware, firmware, and/or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, and/or a magneto-optic disk), a solid state drive (SSD), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a component for determining location (e.g., a global positioning system (GPS) component) and/or a sensor (e.g., an accelerometer, a gyroscope, an actuator, another type of positional or environmental sensor, and/or the like). Output component 360 includes a component that provides output information from device 300 (via, e.g., a display, a speaker, a haptic feedback component, an audio or visual indicator, and/or the like).

Communication interface 370 includes a transceiver-like component (e.g., a transceiver, a separate receiver, a separate transmitter, and/or the like) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. As used herein, the term "computer-readable medium" refers to a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The quantity and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
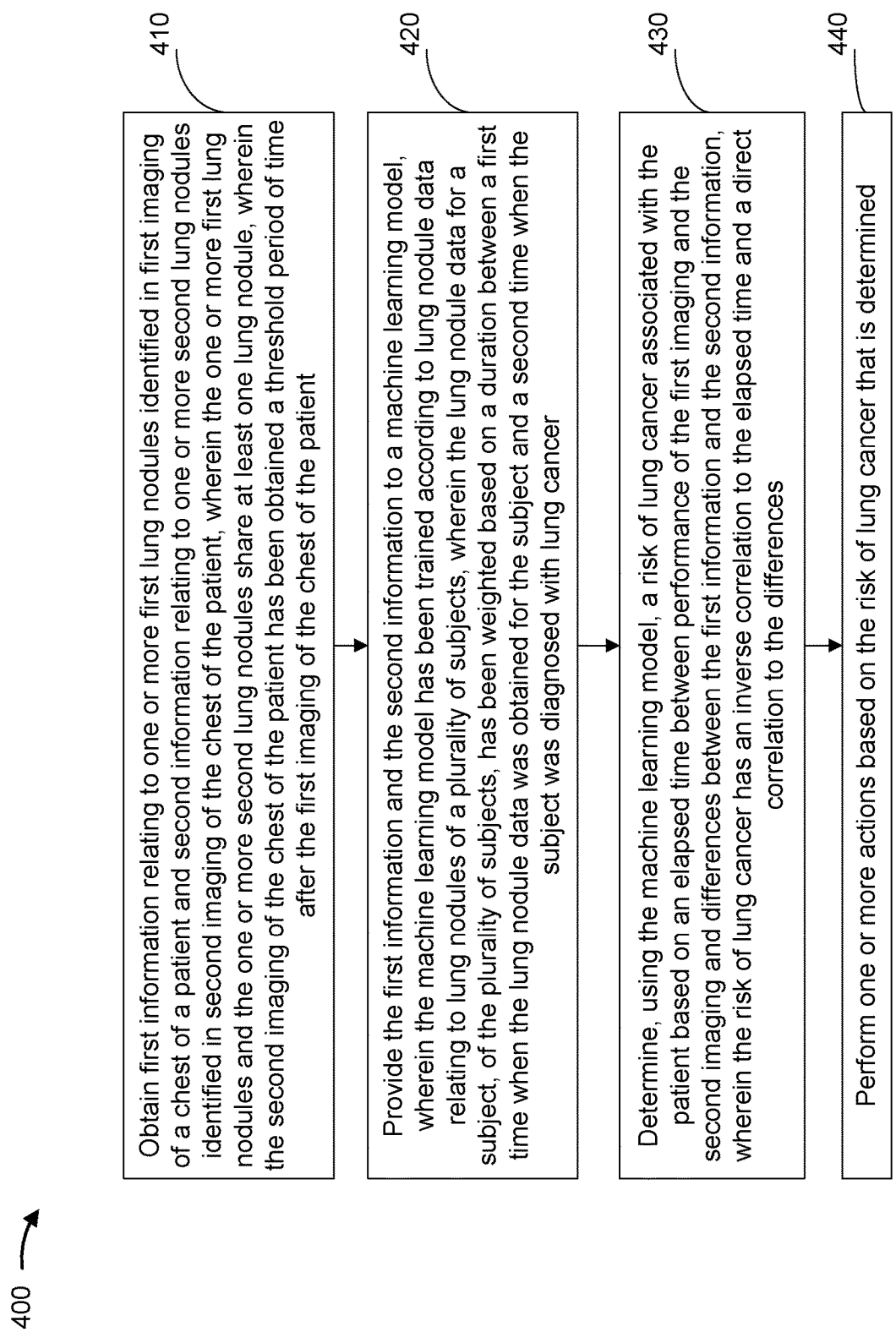
FIGS. 4-6 are flowcharts of example processes for lung cancer prediction.

FIG. 4 is a flow chart of an example process 400 for lung cancer prediction. In some implementations, one or more process blocks of FIG. 4 may be performed by a risk prediction platform (e.g., risk prediction platform 220). In some implementations, one or more process blocks of FIG. 4 may be performed by another device or a group of devices separate from or including the risk prediction platform, such as a user device (e.g., user device 210), or the like.

As shown in FIG. 4, process 400 may include obtaining first information relating to one or more first lung nodules identified in first imaging of a chest of a patient and second information relating to one or more second lung nodules identified in second imaging of the chest of the patient, wherein the one or more first lung nodules and the one or more second lung nodules share at least one lung nodule, and wherein the second imaging of the chest of the patient has been obtained a threshold period of time after the first imaging of the chest of the patient (block 410). For example, the risk prediction platform (e.g., using computing resource 225, processor 320, memory 330, storage component 340, input component 350, communication interface 370, and/or the like) may obtain first information relating to one or more first lung nodules identified in first imaging of a chest of a patient and second information relating to one or more second lung nodules identified in second imaging of the chest of the patient, as described above. In some implementations, the one or more first lung nodules and the one or more second lung nodules share at least one lung nodule. In some implementations, the second imaging of the chest of the patient has been obtained a threshold period of time after the first imaging of the chest of the patient.

As further shown in FIG. 4, process 400 may include providing the first information and the second information to a machine learning model, wherein the machine learning model has been trained according to lung nodule data relating to lung nodules of a plurality of subjects, and wherein the lung nodule data for a subject, of the plurality of subjects, has been weighted based on a duration between a first time when the lung nodule data was obtained for the subject and a second time when the subject was diagnosed with lung cancer (block 420). For example, the risk prediction platform (e.g., using computing resource 225, processor 320, memory 330, storage component 340, and/or the like) may provide the first information and the second information to a machine learning model, as described above. In some implementations, the machine learning model has been trained according to lung nodule data relating to lung nodules of a plurality of subjects. In some implementations, the lung nodule data for a subject, of the plurality of subjects, has been weighted based on a duration between a first time when the lung nodule data was obtained for the subject and a second time when the subject was diagnosed with lung cancer.

As further shown in FIG. 4, process 400 may include determining, using the machine learning model, a risk of lung cancer associated with the patient based on an elapsed time between performance of the first imaging and the second imaging and differences between the first information and the second information, wherein the risk of lung cancer has an inverse correlation to the elapsed time and a direct correlation to the differences (block 430). For example, the risk prediction platform (e.g., using computing resource 225, processor 320, memory 330, storage component 340, and/or the like) may determine, using the machine learning model, a risk of lung cancer associated with the patient based on an elapsed time between performance of the first imaging and the second imaging and differences between the first information and the second information, as described above. In some implementations, the risk of lung cancer has an inverse correlation to the elapsed time and a direct correlation to the differences.

As further shown in FIG. 4, process 400 may include performing one or more actions based on the risk of lung cancer that is determined (block 440). For example, the risk prediction platform (e.g., using computing resource 225, processor 320, memory 330, storage component 340, input component 350, output component 360, communication interface 370, and/or the like) may perform one or more actions based on the risk of lung cancer that is determined, as described above.

Process 400 may include additional implementations, such as any single implementation or any combination of implementations described below and/or in connection with one or more other processes described elsewhere herein.

In a first implementation, the first imaging of the chest of the patient is a first CT scan of the chest of the patient and the second imaging of the chest of the patient is a second CT scan of the chest of the patient. In a second implementation, alone or in combination with the first implementation, obtaining the first information and the second information comprises utilizing computer vision on the first imaging to obtain the first information and utilizing computer vision on the second imaging to obtain the second information.

In a third implementation, alone or in combination with one or more of the first and second implementations, the first information relating to the one or more first lung nodules or the second information relating to the one or more second lung nodules relates to one or more of a size of a nodule, a location of a nodule, an attenuation of a nodule, or a spiculated margin of a nodule.

In a fourth implementation, alone or in combination with one or more of the first through third implementations, the one or more actions include transmitting information identifying the risk of lung cancer associated with the patient to a user device associated with a care provider for the patient. In a fifth implementation, alone or in combination with one or more of the first through fourth implementations, the one or more actions include determining a recommendation for treating the patient based on a degree of the risk of lung cancer associated with the patient, and transmitting information identifying the recommendation to a user device associated with a care provider for the patient.

In a sixth implementation, alone or in combination with one or more of the first through fifth implementations, determining the risk of lung cancer associated with the patient comprises determining the risk of lung cancer associated with the patient and a survival estimate associated with the patient.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
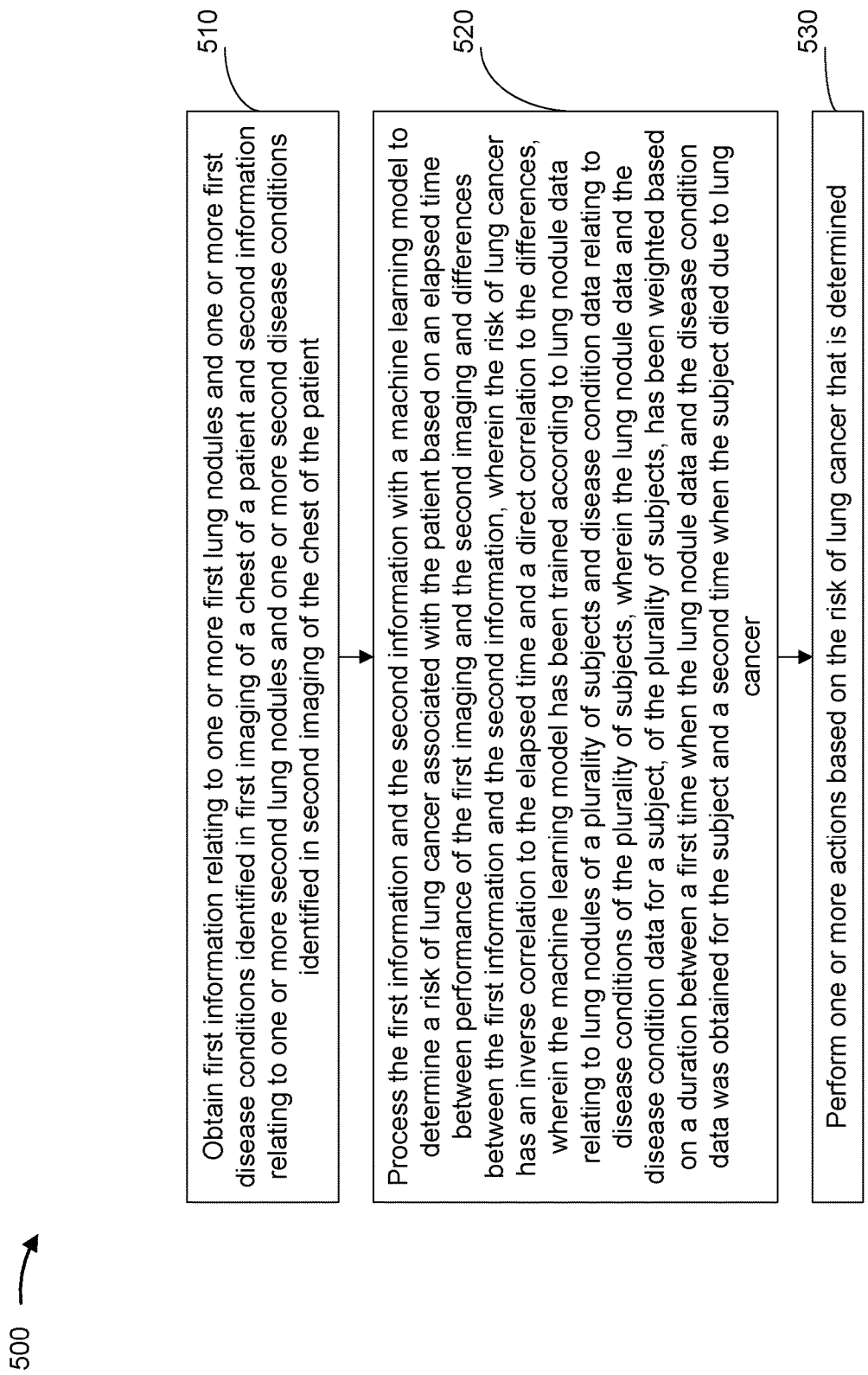

FIG. 5 is a flow chart of an example process 500 for lung cancer prediction. In some implementations, one or more process blocks of FIG. 5 may be performed by a risk prediction platform (e.g., risk prediction platform 220). In some implementations, one or more process blocks of FIG. 5 may be performed by another device or a group of devices separate from or including the risk prediction platform, such as a user device (e.g., user device 210), or the like.

As shown in FIG. 5, process 500 may include obtaining first information relating to one or more first lung nodules and one or more first disease conditions identified in first imaging of a chest of a patient and second information relating to one or more second lung nodules and one or more second disease conditions identified in second imaging of the chest of the patient (block 510). For example, the risk prediction platform (e.g., using computing resource 225, processor 320, memory 330, storage component 340, input component 350, communication interface 370, and/or the like) may obtain first information relating to one or more first lung nodules and one or more first disease conditions identified in first imaging of a chest of a patient and second information relating to one or more second lung nodules and one or more second disease conditions identified in second imaging of the chest of the patient, as described above.

As further shown in FIG. 5, process 500 may include processing the first information and the second information with a machine learning model to determine a risk of lung cancer associated with the patient based on an elapsed time between performance of the first imaging and the second imaging and differences between the first information and the second information, wherein the risk of lung cancer has an inverse correlation to the elapsed time and a direct correlation to the differences, wherein the machine learning model has been trained according to lung nodule data relating to lung nodules of a plurality of subjects and disease condition data relating to disease conditions of the plurality of subjects, and wherein the lung nodule data and the disease condition data for a subject, of the plurality of subjects, has been weighted based on a duration between a first time when the lung nodule data and the disease condition data was obtained for the subject and a second time when the subject died due to lung cancer (block 520). For example, the risk prediction platform (e.g., using computing resource 225, processor 320, memory 330, storage component 340, and/or the like) may process the first information and the second information with a machine learning model to determine a risk of lung cancer associated with the patient based on an elapsed time between performance of the first imaging and the second imaging and differences between the first information and the second information, as described above. In some implementations, the risk of lung cancer has an inverse correlation to the elapsed time and a direct correlation to the differences. In some implementations, the machine learning model has been trained according to lung nodule data relating to lung nodules of a plurality of subjects and disease condition data relating to disease conditions of the plurality of subjects. In some implementations, the lung nodule data and the disease condition data for a subject, of the plurality of subjects, has been weighted based on a duration between a first time when the lung nodule data and the disease condition data was obtained for the subject and a second time when the subject died due to lung cancer.

As further shown in FIG. 5, process 500 may include performing one or more actions based on the risk of lung cancer that is determined (block 530). For example, the risk prediction platform (e.g., using computing resource 225, processor 320, memory 330, storage component 340, input component 350, output component 360, communication interface 370, and/or the like) may perform one or more actions based on the risk of lung cancer that is determined, as described above.

Process 500 may include additional implementations, such as any single implementation or any combination of implementations described below and/or in connection with one or more other processes described elsewhere herein.

In a first implementation, the one or more first disease conditions or the one or more second disease conditions relate to one or more of emphysema, thoracic aortic aneurysm, aortic dissection, marked cardiomegaly, pulmonary hypertension, coronary artery calcifications, or valvular calcifications. In a second implementation, alone or in combination with the first implementation, the first information relating to the one or more first disease conditions or the second information relating to the one or more second disease conditions relates to one of a presence of a disease condition or an absence of a disease condition. In a third implementation, alone or in combination with one or more of the first and second implementations, the one or more first lung nodules are included in the one or more second lung nodules.

In a fourth implementation, alone or in combination with one or more of the first through third implementations, performing the one or more actions comprises determining a recommendation for treating the patient based on a degree of the risk of lung cancer associated with the patient, and transmitting information identifying the recommendation to a user device associated with a care provider for the patient. In a fifth implementation, alone or in combination with one or more of the first through fourth implementations, the second imaging of the chest of the patient was obtained a threshold period of time after the first imaging of the chest of the patient.

In a sixth implementation, alone or in combination with one or more of the first through fifth implementations, processing the first information and the second information with the machine learning model to determine the risk of lung cancer associated with the patient comprises processing the first information and the second information with the machine learning model to determine the risk of lung cancer associated with the patient and to generate a Kaplan-Meier curve representing probabilities that the patient will be free of lung cancer over a time period.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
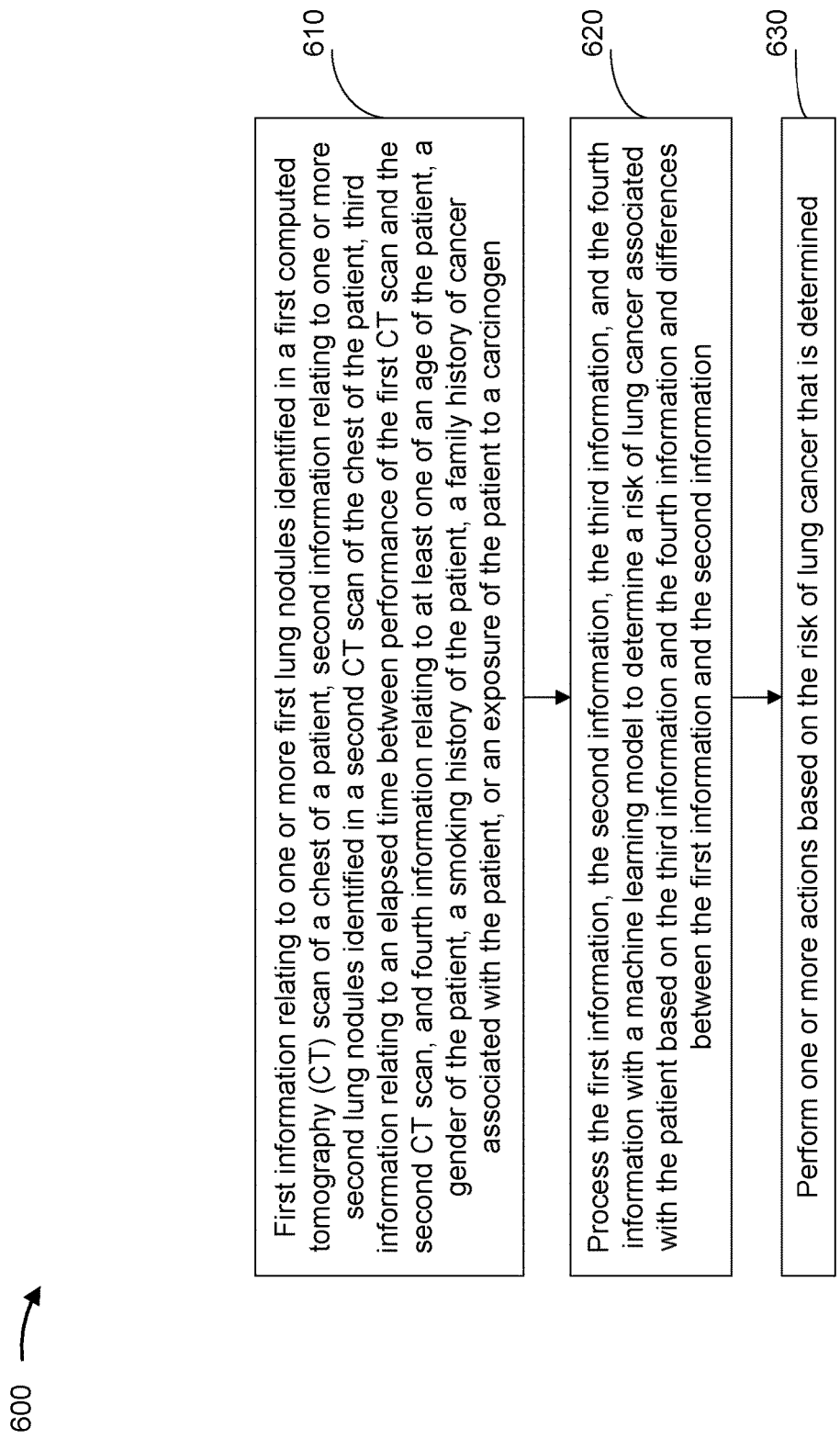

FIG. 6 is a flow chart of an example process 600 for lung cancer prediction. In some implementations, one or more process blocks of FIG. 6 may be performed by a risk prediction platform (e.g., risk prediction platform 220). In some implementations, one or more process blocks of FIG. 6 may be performed by another device or a group of devices separate from or including the risk prediction platform, such as a user device (e.g., user device 210), or the like.

As shown in FIG. 6, process 600 may include obtaining first information relating to one or more first lung nodules identified in a first CT scan of a chest of a patient, second information relating to one or more second lung nodules identified in a second CT scan of the chest of the patient, third information relating to an elapsed time between performance of the first CT scan and the second CT scan, and fourth information relating to at least one of an age of the patient, a gender of the patient, or a smoking history of the patient (block 610). For example, the risk prediction platform (e.g., using computing resource 225, processor 320, memory 330, storage component 340, input component 350, communication interface 370, and/or the like) may obtain first information relating to one or more first lung nodules identified in a first CT scan of a chest of a patient, second information relating to one or more second lung nodules identified in a second CT scan of the chest of the patient, third information relating to an elapsed time between performance of the first CT scan and the second CT scan, and fourth information relating to at least one of an age of the patient, a gender of the patient, a smoking history of the patient a family history of cancer associated with the patient, or an exposure of the patient to a carcinogen, as described above.

As further shown in FIG. 6, process 600 may include processing the first information, the second information, the third information, and the fourth information with a machine learning model to determine a risk of lung cancer associated with the patient based on the third information and the fourth information and differences between the first information and the second information (block 620). For example, the risk prediction platform (e.g., using computing resource 225, processor 320, memory 330, storage component 340, and/or the like) may process the first information, the second information, the third information, and the fourth information with a machine learning model to determine a risk of lung cancer associated with the patient based on the third information and the fourth information and differences between the first information and the second information, as described above.

As further shown in FIG. 6, process 600 may include performing one or more actions based on the risk of lung cancer that is determined (block 630). For example, the risk prediction platform (e.g., using computing resource 225, processor 320, memory 330, storage component 340, input component 350, output component 360, communication interface 370, and/or the like) may perform one or more actions based on the risk of lung cancer that is determined, as described above.

Process 600 may include additional implementations, such as any single implementation or any combination of implementations described below and/or in connection with one or more other processes described elsewhere herein.

In a first implementation, obtaining the first information and the second information comprises utilizing computer vision on the first CT scan to obtain the first information and utilizing computer vision on the second CT scan to obtain the second information. In a second implementation, alone or in combination with the first implementation, the first information relating to the one or more first lung nodules or the second information relating to the one or more second lung nodules relates to one or more of a size of a nodule, a location of a nodule, an attenuation of a nodule, or a spiculated margin of a nodule. In a third implementation, alone or in combination with one or more of the first and second implementations, the first information relating to the one or more first lung nodules or the second information relating to the one or more second lung nodules relates to at least one of whether a nodule of the one or more first lung nodules is included in the one or more second lung nodules, or whether a nodule of the one or more second lung nodules is included in the one or more first lung nodules.

In a fourth implementation, alone or in combination with one or more of the first through third implementations, performing the one or more actions comprises transmitting information identifying the risk of lung cancer associated with the patient to a user device associated with a care provider for the patient.

In a fifth implementation, alone or in combination with one or more of the first through fourth implementations, the machine learning model has been trained according to lung nodule data relating to lung nodules of a plurality of subjects and disease condition data relating to disease conditions of the plurality of subjects, wherein the lung nodule data and the disease condition data for a subject, of the plurality of subjects, has been weighted based on a first duration between a first time when the lung nodule data and the disease condition data was obtained for the subject and a second time when the subject was diagnosed with lung cancer, and a second duration between the first time and a third time when the subject died due to lung cancer.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

Certain user interfaces have been described herein. A user interface may include a graphical user interface, a non-graphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, and/or the like). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
   obtaining, by a device, first information relating to one or more first lung nodules identified in first imaging of a chest of a patient and second information relating to one or more second lung nodules identified in second imaging of the chest of the patient,
      wherein the one or more first lung nodules and the one or more second lung nodules share at least one lung nodule,
      wherein the second imaging of the chest of the patient has been obtained a threshold period of time after the first imaging of the chest of the patient;
   providing, by the device, the first information and the second information to a machine learning model,
      wherein the machine learning model has been trained according to lung nodule data relating to lung nodules of a plurality of subjects,
         wherein the lung nodule data for a subject, of the plurality of subjects, has been weighted based on a duration between a first time when the lung nodule data was obtained for the subject and a second time when the subject was diagnosed with lung cancer;

determining, by the device and using the machine learning model, a risk of lung cancer associated with the patient based on an elapsed time between performance of the first imaging and the second imaging and differences between the first information and the second information,
wherein the risk of lung cancer has an inverse correlation to the elapsed time and a direct correlation to the differences; and performing, by the device, one or more actions based on the risk of lung cancer that is determined.

2. The method of claim 1, wherein the first imaging of the chest of the patient is a first computed tomography (CT) scan of the chest of the patient and the second imaging of the chest of the patient is a second CT scan of the chest of the patient.

3. The method of claim 1, wherein obtaining the first information and the second information comprises:
utilizing computer vision on the first imaging to obtain the first information and utilizing computer vision on the second imaging to obtain the second information.

4. The method of claim 1, wherein the first information relating to the one or more first lung nodules or the second information relating to the one or more second lung nodules relates to one or more of:
a size of a nodule,
a location of a nodule,
an attenuation of a nodule, or
a spiculated margin of a nodule.

5. The method of claim 1, wherein the one or more actions include transmitting information identifying the risk of lung cancer associated with the patient to a user device associated with a care provider for the patient.

6. The method of claim 1, wherein the one or more actions include:
determining a recommendation for treating the patient based on a degree of the risk of lung cancer associated with the patient; and
transmitting information identifying the recommendation to a user device associated with a care provider for the patient.

7. The method of claim 1, wherein determining the risk of lung cancer associated with the patient comprises:
determining the risk of lung cancer associated with the patient and survival estimate associated with the patient.

8. A device, comprising:
one or more memories; and
one or more processors, communicatively coupled to the one or more memories, to:
obtain first information relating to one or more first lung nodules and one or more first disease conditions identified in first imaging of a chest of a patient and second information relating to one or more second lung nodules and one or more second disease conditions identified in second imaging of the chest of the patient;
process the first information and the second information with a machine learning model to determine a risk of lung cancer associated with the patient based on an elapsed time between performance of the first imaging and the second imaging and differences between the first information and the second information,
wherein the risk of lung cancer has an inverse correlation to the elapsed time and a direct correlation to the differences,
wherein the machine learning model has been trained according to lung nodule data relating to lung nodules of a plurality of subjects and disease condition data relating to disease conditions of the plurality of subjects,
wherein the lung nodule data and the disease condition data for a subject, of the plurality of subjects, has been weighted based on a duration between a first time when the lung nodule data and the disease condition data was obtained for the subject and a second time when the subject died due to lung cancer; and
perform one or more actions based on the risk of lung cancer that is determined.

9. The device of claim 8, wherein the one or more first disease conditions or the one or more second disease conditions relate to one or more of emphysema, thoracic aortic aneurysm, aortic dissection, marked cardiomegaly, pulmonary hypertension, coronary artery calcifications, or valvular calcifications.

10. The device of claim 8, wherein the first information relating to the one or more first disease conditions or the second information relating to the one or more second disease conditions relates to one of a presence of a disease condition or an absence of a disease condition.

11. The device of claim 8, wherein the one or more first lung nodules are included in the one or more second lung nodules.

12. The device of claim 8, wherein the one or more processors, when performing the one or more actions, are to:
determine a recommendation for treating the patient based on a degree of the risk of lung cancer associated with the patient; and
transmit information identifying the recommendation to a user device associated with a care provider for the patient.

13. The device of claim 8, wherein the second imaging of the chest of the patient was obtained a threshold period of time after the first imaging of the chest of the patient.

14. The device of claim 8, wherein the one or more processors, when processing the first information and the second information with the machine learning model to determine the risk of lung cancer associated with the patient, are to:
process the first information and the second information with the machine learning model to determine the risk of lung cancer associated with the patient and to generate a Kaplan-Meier curve representing probabilities that the patient will be free of lung cancer over a time period.

15. A non-transitory computer-readable medium storing instructions, the instructions comprising:
one or more instructions that, when executed by one or more processors, cause the one or more processors to:
obtain:
first information relating to one or more first lung nodules identified in a first computed tomography (CT) scan of a chest of a patient,
second information relating to one or more second lung nodules identified in a second CT scan of the chest of the patient,
third information relating to an elapsed time between performance of the first CT scan and the second CT scan, and fourth information relating to at least one of an age of the patient, a gender of the patient, a smoking history of the patient, a family history of cancer associated with the patient, or an exposure of the patient to a carcinogen;

process the first information, the second information, the third information, and the fourth information with a machine learning model to determine a risk of lung cancer associated with the patient based on the third information and the fourth information and differences between the first information and the second information; and perform one or more actions based on the risk of lung cancer that is determined.

16. The non-transitory computer-readable medium of claim 15, wherein the one or more instructions, that cause the one or more processors to obtain the first information and the second information, cause the one or more processors to:
utilize computer vision on the first CT scan to obtain the first information and utilize computer vision on the second CT scan to obtain the second information.

17. The non-transitory computer-readable medium of claim 15, wherein the first information relating to the one or more first lung nodules or the second information relating to the one or more second lung nodules relates to one or more of:
a size of a nodule,
a location of a nodule,
an attenuation of a nodule, or
a spiculated margin of a nodule.

18. The non-transitory computer-readable medium of claim 15, wherein the first information relating to the one or more first lung nodules or the second information relating to the one or more second lung nodules relates to at least one of:
whether a nodule of the one or more first lung nodules is included in the one or more second lung nodules, or
whether a nodule of the one or more second lung nodules is included in the one or more first lung nodules.

19. The non-transitory computer-readable medium of claim 15, wherein the one or more instructions, that cause the one or more processors to perform the one or more actions, cause the one or more processors to:
transmit information identifying the risk of lung cancer associated with the patient to a user device associated with a care provider for the patient.

20. The non-transitory computer-readable medium of claim 15, wherein the machine learning model has been trained according to lung nodule data relating to lung nodules of a plurality of subjects and disease condition data relating to disease conditions of the plurality of subjects,
wherein the lung nodule data and the disease condition data for a subject, of the plurality of subjects, has been weighted based on a first duration between a first time when the lung nodule data and the disease condition data was obtained for the subject and a second time when the subject was diagnosed with lung cancer, and a second duration between the first time and a third time when the subject died due to lung cancer.

\* \* \* \* \*